United States Patent
Shalaby et al.

(10) Patent No.: US 8,815,975 B2
(45) Date of Patent: Aug. 26, 2014

(54) CYANOACRYLATE TISSUE ADHESIVE FORMULATIONS WITH MULTIPURPOSE RHEOLOGY MODIFIERS

(75) Inventors: Shalaby W. Shalaby, Anderson, SC (US); Michael Aaron Vaughn, Clemson, SC (US); James M. Lindsay, III, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 52 days.

(21) Appl. No.: 12/386,401

(22) Filed: Apr. 18, 2009

(65) Prior Publication Data

US 2009/0264555 A1 Oct. 22, 2009

Related U.S. Application Data

(60) Provisional application No. 61/124,692, filed on Apr. 18, 2008.

(51) Int. Cl.
| | | |
|---|---|---|
| A61L 24/00 | (2006.01) | |
| A61K 8/72 | (2006.01) | |
| C08G 18/42 | (2006.01) | |
| C08L 67/00 | (2006.01) | |
| C08G 63/08 | (2006.01) | |
| C08G 63/44 | (2006.01) | |
| A61L 24/06 | (2006.01) | |
| A61L 24/04 | (2006.01) | |

(52) U.S. Cl.
CPC *A61L 24/06* (2013.01); *A61L 24/04* (2013.01)
USPC ........... 523/118; 523/105; 523/113; 524/539; 524/612; 525/418; 528/354; 528/362

(58) Field of Classification Search
USPC .......................................................... 523/118
See application file for complete search history.

(56) References Cited

U.S. PATENT DOCUMENTS

| | | | |
|---|---|---|---|
| 4,125,494 A | 11/1978 | Schoenberg et al. | |
| 5,350,798 A | 9/1994 | Linden et al. | |
| 5,530,037 A * | 6/1996 | McDonnell et al. | 522/79 |
| 6,299,631 B1 | 10/2001 | Shalaby | |
| 6,433,096 B1 | 8/2002 | Hickey et al. | |
| 6,512,023 B1 | 1/2003 | Malofsky et al. | |
| 6,699,940 B2 * | 3/2004 | Shalaby | 525/308 |
| 6,723,114 B2 * | 4/2004 | Shalaby | 606/214 |
| 6,977,278 B1 * | 12/2005 | Misiak | 524/315 |
| 7,083,634 B2 | 8/2006 | Shalaby | |
| 7,138,464 B2 | 11/2006 | Shalaby | |
| 7,351,426 B2 | 4/2008 | Shalaby et al. | |
| 2004/0132923 A1 * | 7/2004 | Shalaby | 525/418 |
| 2004/0133237 A1 * | 7/2004 | Shalaby | 606/230 |
| 2006/0216266 A1 * | 9/2006 | Liu | 424/78.27 |
| 2006/0241226 A1 * | 10/2006 | Bachon et al. | 524/315 |

* cited by examiner

*Primary Examiner* — Peter F Godenschwager
*Assistant Examiner* — David Karst

(57) ABSTRACT

Absorbable and non-absorbable cyanoacrylate tissue adhesive/sealant formulations include at least one multipurpose carboxylic, acid-bearing C-succinylated polymeric rheology modifier capable of increasing the viscosity of the liquid formulation, while controlling the anionic polymerization of the cyanoacrylate monomers and increasing the compliance of the cured solid adhesive.

3 Claims, No Drawings

CYANOACRYLATE TISSUE ADHESIVE FORMULATIONS WITH MULTIPURPOSE RHEOLOGY MODIFIERS

This application claims the benefit of prior provisional application Ser. No. 61/124,692, filed Apr. 18, 2008.

FIELD OF THE INVENTION

This invention is directed toward liquid cyanoacrylate tissue adhesive formulations comprising at least one carboxylic acid-bearing multipurpose heterochain polymeric rheology modifier capable of increasing the viscosity of the liquid cyanoacrylate monomers, increasing the compliance of the cured tissue adhesive, and shielding against premature anionic polymerization of the cyanoacrylate monomers. The multipurpose rheology modifiers can be tailored for use with one or more cyanoacrylate monomer to yield absorbable or non-absorbable tissue adhesive formulations which can be sterilized by filtration or radiochemically.

BACKGROUND OF THE INVENTION

The prior art on cyanoacrylate tissue adhesives has covered many aspects relating to monomer synthesis, preparation and the stabilization against premature anionic and free-radical polymerization of absorbable and non-absorbable tissue adhesive formulations, as well as their tailored modification for effective use, mostly, for topical applications in animals and humans. However, since the development of absorbable cyanoacrylate tissue adhesives, a great deal of interest was directed to the use of polymeric modifiers to impart certain clinically useful properties, which are most pertinent to the instant invention. More specifically, the prior art on absorbable alkoxyalkyl cyanoacrylate-based tissue adhesive/sealant formulations dealt with polymeric modifiers such as (1) oxalate polymers of triethylene glycol (U.S. Pat. No. 5,350,798); (2) oxalate polymers of polyethylene glycols having an average degree of polymerization in excess of 4 (U.S. Pat. No. 6,723,114); (3) poly(2-ethylhexyl methacrylate), poly(vinyl acetate) and lactic acid-caprolactone copolymers (U.S. Pat. No. 6,433,096; and (4) trimethylene carbonate-based polymers (U.S. Pat. No. 6,299,631). The prior art also dealt with stabilized cyanoacrylate-based compositions comprising one or more acidic compound(s) or precursor(s) thereof to maximize the stability of adhesives during storage regardless of the chemical structure of the ester groups (U.S. Pat. Nos. 7,083,634; 6,512,023; 4,125,494). All the absorbable tissue adhesive formulations disclosed in the prior art were comprised predominantly of alkoxy cyanoacrylate monomers which are known to undergo absorption in the biologic environment. The presence of the hydrophilic ether linkage in the alkoxyalkyl cyanoacrylates made them different from all known hydrophobic alkyl cyanoacrylates, in terms of the superior spreadability on biological tissues. This, in turn, minimizes the required adhesive formulation mass per unit area of treated biological tissues. Meanwhile, certain members of alkyl cyanoacrylate groups can provide a distinctly strong adhesive joint upon anionic polymerization in the biologic environment when used as non-absorbable tissue adhesives. This prompted blending small amounts of one or more alkyl cyanoacrylate(s) with established absorbable tissue adhesive formulations of the prior art to improve the initial adhesive joint strength and allow modulating the retention of the adhesive joint holding strength profile, in vivo, without compromising, significantly, the spreadability of the liquid formulation on biological tissues and the bioabsorption of the polymerized solid products as described in U.S. Pat. No. 7,351,426. More specifically, the latter patent dealt with absorbable tissue adhesive compositions comprising one or more alkoxyalkyl cyanoacrylate-based formulation(s) as a major component and one or more alkyl cyanoacrylate(s) as the minor component of said compositions.

Collective analysis of the prior art, discussed above, dealing with both absorbable and non-absorbable cyanoacrylate tissue adhesive/sealant formulations as it pertains specifically to acidic or acid-forming additives used for shielding against premature anionic polymerization and polymeric modifiers indicate that (1) virtually all the acidic or acid-forming additives are simple organic compounds; (2) all polymeric modifiers comprise essentially neutral polymeric chains; and (3) the acidic (e.g., acetic acid and mineral acids) or acid-forming additives and polymeric modifiers are used independently to achieve two distinctly different functions. Thus, consistent calls to simplify clinically important cyanoacrylate tissue adhesive formulations and recent availability of functionalized and, particularly, carboxylic acid-bearing copolyester(s) (U.S. Pat. No. 7,138,464) prompted the exploration of the subject of the instant invention, dealing with the use of multipurpose polymeric rheology modifiers that can also shield against premature polymerization.

SUMMARY OF THE INVENTION

This invention deals in general with a liquid cyanoacrylate tissue/sealant adhesive formulation comprising at least one multipurpose carboxylic acid-bearing C-succinylated polymeric rheology modifier capable of increasing the viscosity of the liquid formulation by at least 5 percent, shielding against premature anionic polymerization of cyanoacrylate monomers, and increasing the compliance of the cured formulation, wherein the C-succinylated polymeric rheology modifier comprises at least one C-succinylated heterochain polymer selected from the group consisting of polyalkylene glycols, triaxial segmented copolyesters, and an aliphatic polyether-esters and wherein the triaxial segmented copolyester comprises a chain molecule comprising a non-crystallizable center derived from at least trimethylene carbonate having, a $T_g$ below 25° C. that is end-grafted with l-lactide or a mixture of l-lactide and other lactones to produce terminal l-lactide-rich segment that exhibits no or a low degree of crystallinity as measured in terms of a heat of fusion of 0 to 20 J/g, and further, wherein the C-succinylated heterochain polymer is made by the step of reacting the heterochain polymer with maleic anhydride under free-radical conditions to introduce succinic anhydride side groups onto the main chain and half-ester end-groups, followed by the step of selective hydrolysis of the anhydride side group to yield succinic acid side groups.

A specific aspect of the invention deals with a liquid cyanoacrylate tissue adhesive/sealant formulations comprising at least one multipurpose carboxylic acid-bearing C-succinylated polymeric rheology modifier capable of increasing the viscosity of the liquid formulation by at least 5 percent, shielding against premature anionic polymerization of cyanoacrylate monomers, and increasing the compliance of the cured formulation, wherein the cyanoacrylate component comprises at least 10 percent by weight of methoxypropyl cyanoacrylate and at least one percent by weight of a polymeric C-succinylated rheology modifier, and wherein said formulation further comprises at least 50 percent by weight of an alkyl cyanoacrylate selected from the group consisting of ethyl, n-butyl, isobutyl, hexyl, and octyl cyanoacrylate, as well as at least two (2) ppm of pyrophosphoric acid.

Another specific aspect of the invention deals with a liquid cyanoacrylate tissue adhesive/sealant formulation comprising at least one multipurpose carboxylic acid-bearing C-succinylated polymeric rheology modifier capable of increasing the viscosity of the liquid formulation by at least 5 percent, shielding against premature anionic polymerization of cyanoacrylate monomers, and increasing the compliance of the cured formulation, wherein the cyanoacrylate component comprises at least 70 percent by weight of a methoxyalkyl cyanoacrylate selected from the group consisting of methoxyethyl, methoxypropyl, methoxybutyl, and ethoxyethyl cyanoacrylate.

A clinically important aspect of the invention deals with a liquid cyanoacrylate tissue adhesive/sealant formulation comprising at least one multipurpose carboxylic acid-bearing C-succinylated polymeric rheology modifier capable of increasing the viscosity of the liquid formulation by at least 5 percent, shielding against premature anionic polymerization of cyanoacrylate monomers, and increasing the compliance of the cured formulation, wherein said formulation absorbs in the biological environment in less than two years, and wherein the cyanoacrylate component comprises at least 70 percent by weight of methoxypropyl cyanoacrylate and a balance of ethyl cyanoacrylate. Alternatively, the cyanoacrylate component is methoxypropyl cyanoacrylate, which comprises at least one percent by weight of a C-succinylated heterochain segmented copolyester, at least 2 ppm of pyrophosphoric acid, and less than 1000 ppm of free-radical scavenger.

A technologically important aspect of this invention deals with a liquid cyanoacrylate tissue adhesive/sealant formulation comprising at least one multipurpose carboxylic acid-bearing C-succinylated polymeric rheology modifier capable of increasing the viscosity of the liquid formulation by at least 5 percent, shielding against premature anionic polymerization of cyanoacrylate monomers, and increasing the compliance of the cured formulation, wherein said formulation is sterilized by high-energy radiation.

Another technologically important aspect of the invention deals with a liquid cyanoacrylate tissue adhesive/sealant formulation comprising at least one multipurpose carboxylic acid-bearing C-succinylated polymeric rheology modifier capable of increasing the viscosity of the liquid formulation by at least 5 percent, shielding against premature anionic polymerization of cyanoacrylate monomers, and increasing the compliance of the cured formulation, wherein said formulation is packaged in a sealed container, placed in a hermetically sealed, virtually impermeable foil pack, pre-loaded with an organic compound capable of radiolytic generation of formaldehyde gas and sterilized radiochemically, using 5-10 kGy of high-energy radiation.

Yet another technologically important aspect of the invention deals with a liquid cyanoacrylate tissue adhesive/sealant formulation comprising at least one multipurpose carboxylic acid-bearing C-succinylated polymeric rheology modifier capable of increasing the viscosity of the liquid formulation by at least 5 percent, shielding against premature anionic polymerization of cyanoacrylate monomers, and increasing the compliance of the cured formulation, wherein said formulation is sterile-filtered into the final package.

DETAILED DESCRIPTION OF PREFERRED EMBODIMENTS

Since the discovery of the cyanoacrylate adhesives, there have been consistent efforts to (1) modulate their fast rate of polymerization, anionically, to prevent premature polymer formation—this entailed the use of simple inorganic and organic components, such as acetic acid and mineral acids; (2) improve their shelf-life—this required the use of additives to shield against anionic and free-radical polymerization, such as free-radical scavengers and simple acids (or acid-producing compounds), such as those noted in 1; (3) to increase their viscosity to facilitate handling and confine their application to the intended site; and (4) lower their stiffness and increasing their compliance after curing to solid forms—this required the use of certain organic esters or polymeric flexible modifier(s) as traditional plasticizers. Unfortunately, in spite of constant attempts to harness the basic attributes of the different cyanoacrylate monomers and to use them effectively as tissue adhesives, there has been a distinct disconnect among the different investigated means to achieve, satisfactorily, important clinical goals. Accordingly, it is the primary objective of this invention to focus on a novel approach to meeting, simultaneously, three of the key requirements for producing clinically useful absorbable and non-absorbable tissue adhesive formulations based on one or more cyanoacrylate monomer(s). In effect, the present invention deals with the use of carboxylic acid-bearing cyanoacrylate-miscible heterochain polymers made of safe organic precursors as polymeric rheology modifiers, which can also function concomitantly to (1) increase the liquid monomer viscosity for ease of handling and application to the intended site; (2) modulate the rate of the anionic polymerization and shield against premature polymerization to allow for a practical shelf-life; and (3) serve as polymeric plasticizers to lower the modulus of the cured (or polymerized) monomers to provide a mechanically compatible solid adhesive having tissue-matching (or close-to-matching) modulus or compliance.

From a chemical perspective, the polymeric rheology modifiers, subject of this invention, are made by reacting heterochain polymers with maleic anhydride under free-radical conditions to yield their C-succinylated derivatives after selective hydrolysis of anhydride side groups as described in a recent disclosure by one of the present inventors (U.S. Pat. No. 7,138,464). The C-succinylated derivatives are designed to have at least one succinic acid group in the chain (i.e., at least two intrachain carboxylic groups). Meanwhile, if the heterochain polymeric precursor contains one or two hydroxyl end-groups, these can undergo acylation by the maleic anhydride to form one or two half-ester end-groups (i.e., one or two carboxylic end-groups). The extent of the C-succinylation can be controlled to provide the desirable frequency of the carboxylic group in the polymer chain. Obviously, as the concentration (or frequency) of carboxylic groups increases within a certain range (beyond this range, excessive C-succinylation can compromise the performance of the modifier), the effectiveness of the C-succinylated polymer in controlling or shielding the anionic polymerization increases. For use in non-absorbable cyanoacrylate tissue adhesive formulations, the heterochain polymeric precursors of the C-succinylated polymers can be of the absorbable or non-absorbable type. On the other hand, for use in absorbable cyanoacrylate tissue adhesive formulations, absorbable heterochain polymers are used as the precursors of the C-succinylated rheology modifiers. Accordingly, the precursors of the absorbable C-succinylated heterochain polymer(s) can be a member of the (1) polyester family, such as copolymers of ε-caprolactone and/or trimethylene carbonate, copolymers of p-dioxanone (or 1,5-dioxapan-2-one), copolymers of l-lactide (or dl-lactide) with ε-caprolactone and/or trimethylene carbonate, polytrimethylene succinate (or related polyalkylene succinates), and polyalkylene oxalate (e.g., polyhexamethylene oxalate, octamethylene oxalate); (2) polyether-ester family, such as copolymer of polyethylene glycol and dicarboxylic acids, polyether glycols (e.g., polyethylene glycol, block copolymer of polyethylene glycol and polypropylene glycol, random copolymers of ethylene oxide, and propylene oxide) end-grafted with at least one cyclic monomer selected from the group consisting of dl-lactide, l-lactide, glycolide, ε-caprolactone, p-dioxanone, 1,5-dioxepan-2-one, and trimethylene carbonate; (3) aliphatic polyethers, such as polyethylene glycol, block copolymers of polyethylene glycol, and polypropylene glycol, random copolymers of ethylene oxide and propylene oxide; and (4) aliphatic polyether-urethanes, polyester urethanes, and polyether-ester-urethanes.

Physically, the polymeric rheology modifier is selected from one or more family(ies) of C-succinylated polymer(s) described above and are (1) miscible in the cyanoacrylate monomer(s); (2) liquids, amorphous solids, or low-melting solids; and (3) absorbable when used for the production of absorbable tissue adhesive formulations (or compositions).

From a clinical perspective, the inventive tissue adhesive/sealant formulation is tailored to spread freely on aqueous surfaces. More specifically, upon applying a liquid formulation onto a wet surgical site, it will spread into a thin adherent film and not a deformed drop. The extent of formulation spreadability can be controlled by incorporating variable amounts of an alkoxy methyl cyanoacrylate (e.g., methoxypropyl cyanoacrylate) or ethyl cyanoacrylate, which are sufficiently compatible with water.

To augment the effectiveness of the carboxylic acid-bearing rheology modifiers in controlling the anionic polymerization, a well-established acidic (or acid-producing) compound that has a similar effect at much lower concentration can be used as in the case of pyrophosphoric acid. Furthermore, to increase the effectiveness against unwanted free-radical polymerization, a small amount of a well-established free-radical scavenger (e.g., hydroquinone or butylated anisole) can be incorporated in the adhesive/sealant formulation (or composition).

Further illustrations of the present invention are provided by the following examples:

Example 1

Preparation of a Typical Precursor, Copolyester (P1) of the Rheology Modifiers (RM)

To prepare a polymeric initiator, the Segment I monomers, trimethylolpropane, and tin(II) 2-ethyl hexanoate were added to a stainless steel reactor equipped for mechanical stirring and vacuum. The contents were dried at 40° C. under vacuum for 1 hour and the pressure equilibrated with dry nitrogen. The contents were stirred to ensure complete mixing and the temperature was raised to 180° C. The reaction was allowed to continue at 180° C. until 50-100% monomer conversion was achieved. The polymeric initiator was then cooled to and maintained at room temperature for approximately 15 hours. The polymeric initiator was then heated to 110° C. and the Segment II monomers were added. The mixture was stirred until the polymeric initiator was dissolved, another equal aliquot of tin(II) 2-ethyl hexanoate was added, and the temperature was raised to 160° C. The contents were stirred for about 30 minutes after the temperature reached 160° C. The stirring was then stopped and the Segment II reaction conditions of Table I were maintained. The composition and polymerization data are outlined in Table I.

Upon completion of the polymerization, the polymer was removed and broken into ~1 in³ pieces. The polymer was then further purified by precipitating its 20% (w/v) DCM solution using 2 parts −60° C. IPA in a commercial blender. The purified polymer was then dried to a constant weight under reduced pressure at temperatures up to 80° C.

TABLE I

Composition and Polymerization Data for Precursor Copolyester P1

| | Composition | | | | | | |
|---|---|---|---|---|---|---|---|
| Polymer Name | Segment I CL/TMC/ G (molar) | Segment II LL/CL/G (molar) | Overall CL/TMC/LL/ G (molar) | Segment I Reaction Time at 180° C. (hr) | Segment II Reaction Time (hr)/ Temp (° C.) | Total Monomer/ Catalyst (moles) | Total Monomer/ Initiator (moles) |
| P1 | 35/14/9 | 34/0/8 | 35/14/34/17 | 10 | 50/140 | 28,000 | 800 |

Example 2

Preparation of Precursor Copolyester P2

This was conducted in a similar manner to that outlined in Example 1. For an initial charge, trimethylolpropane (8.4× $10^{-3}$ moles) was added to a 1 L, glass kettle equipped for mechanical stirring and vacuum. The contents were heated to 40° C. under vacuum and conditions were maintained for 1 hour. For a second charge, trimethylene carbonate (2.94 moles) was added and the contents were heated to 100° C. while stirring. For a third charge, tin(II) 2-ethyl hexanoate (4.20×$10^{-4}$ moles) as 0.2M in toluene was added and the contents were heated to 160° C. while stirring. Conditions were maintained until practically complete monomer conversion was achieved.

Example 3

Preparation of Precursor Copolyester P3

This was conducted in a similar manner to that outlined in Example 1. For an initial charge, poly(ethylene glycol-ran-propylene glycol) ($M_n$=12 kDa) (8.75×$10^{-3}$ moles) was added to a 1 L, glass kettle equipped for mechanical stirring and vacuum. The contents were heated to 140° C. under vacuum and conditions were maintained for 1 hour. The contents were allowed to cool to 60° C. For a second charge, trimethylene carbonate (1.91 moles) was added and the contents were heated to 100° C. while stirring. For a third charge, tin(II) 2-ethyl hexanoate (2.73×$10^{-4}$ moles) as 0.2M in toluene was added and the contents were heated to 160° C. while stirring. Conditions were maintained until practically complete monomer conversion was achieved.

Example 4

Characterization of Precursor Copolyesters P1 to P3

Using traditional analytical methods, P1 to P3 were characterized and pertinent data are summarized in Table II.

TABLE II

Analytical Data of P1 to P3

| Precursor Copolyester | GPC Data $M_n$ (kDa) | $M_w$ (kDa) | Inherent Viscosity (dL/g) |
| --- | --- | --- | --- |
| P1 | 96 | 185 | 1.39 |
| P2 | 37 | 92 | 0.95 |
| P3 | 42 | 79 | 0.85 |

Example 5

Preparation and Characterization of a Typical Rheology Modifier (RM1) Using Precursor Copolyester P1 Through C-Succinylation The first stage of the C-succinylation reaction for P1 was conducted in solution using a 1:5 (w/v) of P1 to 1,4-dioxane. The polymer was dissolved at 50° C. The reaction was completed at 75° C. The weight fraction of the maleic anhydride added to the polymer 63.6%. The weight fraction of the benzoyl peroxide to the polymer was 6.0%. Both of these charges were divided into six individual charges, which were added on an hourly basis starting when the reaction temperature reached 75° C. The total reaction time was eight hours. The 1,4 dioxanone was removed by extraction using iced water. The polymer was poured into a blender with iced water and mixed using a 1:20 (v:v) polymer solution to iced water ratio. The mixture was separated by vacuum filtration. The remaining polymer was rinsed in a 1:10 (w/v) ratio of IPA. This was repeated three times. The polymer then dried to constant weight under reduced pressure at up to 80° C. In Table III, the analytical data of the succinylated RM1 are summarized.

TABLE III

Analytical Results of a Typical C-succinylated Product (RM1)

| Polymer Name | GPC Data Mn (kDa) | Mw (kDa) | Inherent Viscosity, dL/g | Acid Equivalents, g/eq |
| --- | --- | --- | --- | --- |
| RM1 | 69 | 154 | 1.27 | 7934 |

Example 6

Preparation and Properties of Absorbable Cyanoacrylate Tissue Adhesive Formulation Using RM1 of Example 5

The adhesive formulation was prepared by mixing of 3% (wt) of RM1 (predried at 80° C. for 3 hours under reduced pressure) in 20/80 (wt) mixture of methoxypropyl cyanoacrylate and butyl cyanoacrylate containing 500 ppm of butylated hydroxyanisole and 3.3 ppm of pyrophosphoric acid. The mixed composition was stirred at 80° C. until a homogenous liquid was obtained. The resulting formulation was shown to have a comparative adhesive viscosity of 25.45 s and an adhesive joint strength of 36.74 N (using the Fabric Peel test). For comparison, a 20/80 (wt) mixture of methoxypropyl to butyl cyanoacrylate monomer indicated a comparative adhesive viscosity of only 3.55 s.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A liquid cyanoacrylate tissue adhesive/sealant formulation comprising:

a mixture of n-butyl cyanoacrylate and methoxypropyl cyanoacrylate or ethyl cyanoacrylate and methoxypropyl cyanoacrylate at a weight ratio ranging between 50/50 and 90/10;

at least one carboxylic acid-bearing C-succinylated heterochain polymeric modifier which is a triaxial segmented copolyester comprising ε-caprolactone, trimethylene carbonate, l-lactide, and glycolide in a molar ratio of 35/14/34/17, the triaxial segmented copolyester being made by the step of reacting the triaxial segmented copolyester with maleic anhydride under free-radical conditions to introduce succinic anhydride side groups onto the main chain and half-ester end-groups, followed by the step of selective hydrolysis of the anhydride side group to yield succinic acid side groups;

at least 2 ppm of an acidic or acid producing compound;

less than 1000 ppm of a free-radical scavenger; and wherein the C-succinylated heterochain polymeric modifier is capable of increasing the viscosity of the liquid formulation by at least 5 percent relative to the mixture of n-butyl cyanoacrylate and methoxypropyl cyanoacrylate or ethyl cyanoacrylate and methoxypropyl cyanoacrylate alone, shielding against premature anionic polymerization of cyanoacrylate monomers, and increasing the compliance of the cured formulation.

2. The formulation of claim 1 which comprises 3 wt % of the carboxylic acid-bearing C-succinylated triaxial segmented copolyester.

3. The formulation of claim 1 wherein the triaxial segmented copolyester is made by polymerizing a first segment comprising ε-caprolactone, trimethylene carbonate and glycolide in a molar ration of 35/14/9 and a second segment comprising l-lactide and glycolide in a molar ratio of 34/8.

* * * * *